(12) United States Patent
Riesner et al.

(10) Patent No.: US 6,498,017 B2
(45) Date of Patent: *Dec. 24, 2002

(54) METHOD FOR MEASURING THE ASSOCIATION OF SUBSTRUCTURES OF PATHOLOGICAL PROTEIN DEPOSITIONS

(75) Inventors: Detlev Riesner, Dormagen; Karin Post, Duesseldorf; Oliver Schaefer, Essen; Martin Pitschke, Velbert; Manfred Eigen; Jan Bieschke, both of Goettingen, all of (DE)

(73) Assignee: Evotec Biosystems AG, Hamburg (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 17 days.

(21) Appl. No.: 09/508,959
(22) PCT Filed: Sep. 18, 1998
(86) PCT No.: PCT/EP98/05958
    § 371 (c)(1),
    (2), (4) Date: May 22, 2000
(87) PCT Pub. No.: WO99/15903
    PCT Pub. Date: Apr. 1, 1999

(65) Prior Publication Data
US 2002/0042121 A1 Apr. 11, 2002

(30) Foreign Application Priority Data
Nov. 28, 1907 (DE) .......................................... 197 52 712
Sep. 19, 1997 (DE) .......................................... 197 41 486
Apr. 28, 1998 (DE) .......................................... 198 18 917

(51) Int. Cl.⁷ .............................. C12Q 1/37; C12Q 1/00
(52) U.S. Cl. ............................................. 435/23; 435/4
(58) Field of Search ....................................... 435/23, 4

(56) References Cited

U.S. PATENT DOCUMENTS 5,270,165 A * 12/1993 Van Norstrand et al. .... 435/7.1

FOREIGN PATENT DOCUMENTS

| WO | WO93/23432 | 11/1993 |
| WO | WO97/10505 | 3/1997 |
| WO | WO97/15685 | 5/1997 |

* cited by examiner

Primary Examiner—Louise N. Leary
(74) Attorney, Agent, or Firm—Jacobson Holman, PLLC

(57) ABSTRACT

A method for the diagnostic detection of diseases associated with protein depositions (pathological protein depositions) by measuring an association of substructures of the pathological protein depositions, structures forming pathological protein depositions, structures corresponding to pathological protein depositions and/or pathological protein depositions as a probe;

to substructures of the pathological protein depositions structures forming pathological protein depositions, structures corresponding to pathological protein deposition and/or pathological protein depositions as targets;

characterized in that the target is detected in liquid phase wherein, in the case of detecting Alzheimer's disease, the liquid phase is obtained from body fluids or is itself a body fluid;

with the proviso that the association of the probe to the target is measured before self-aggregation of the probe predominates.

27 Claims, 13 Drawing Sheets

Screening for active substances
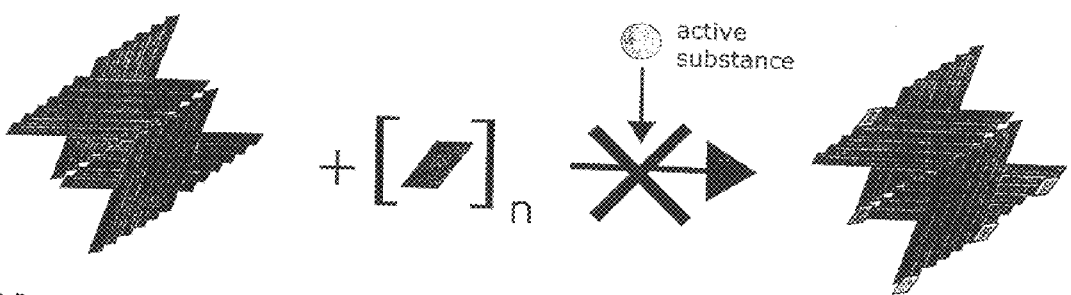
A) Potential active substance blocks the association of labeled probes to amyloid aggregates
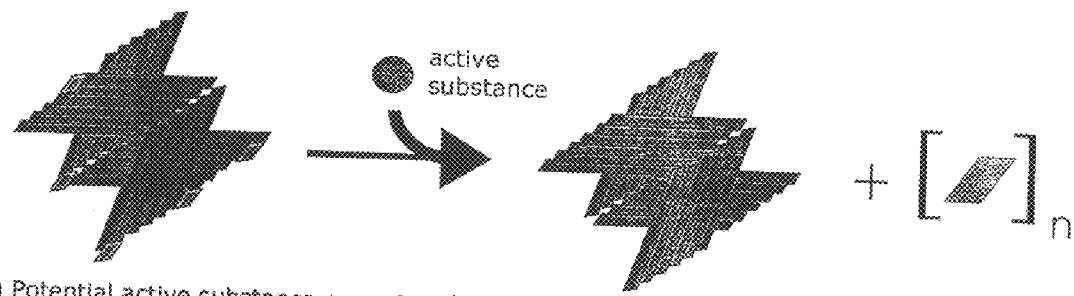
B) Potential active substance promotes the association of labeled probes to amyloid aggregates
Figure 8

Figure 9
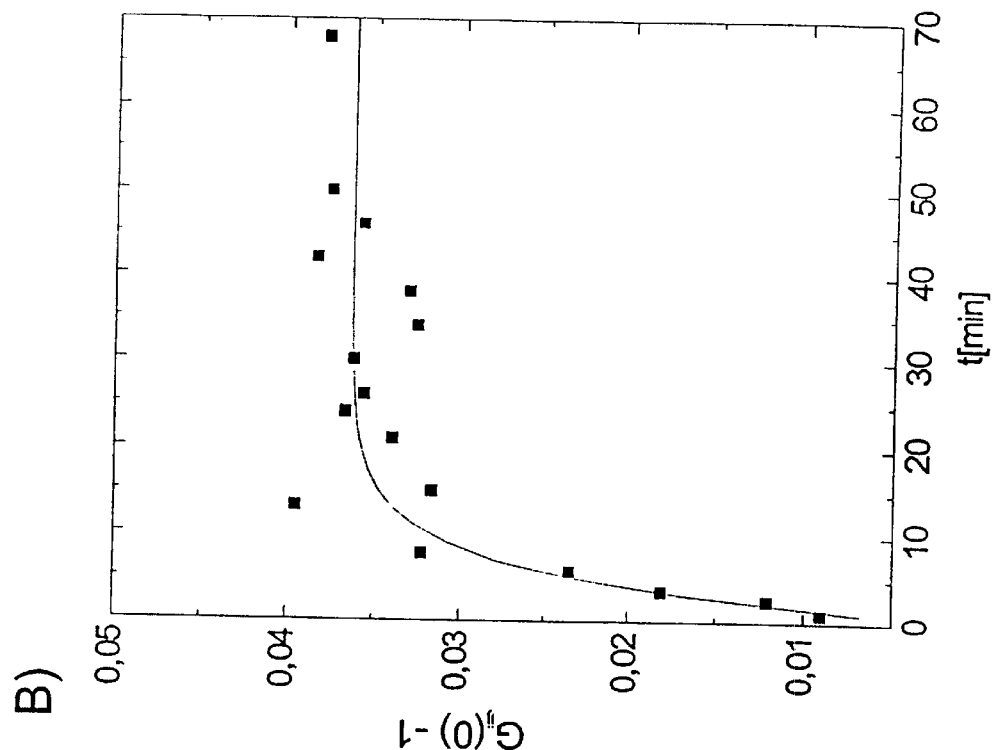
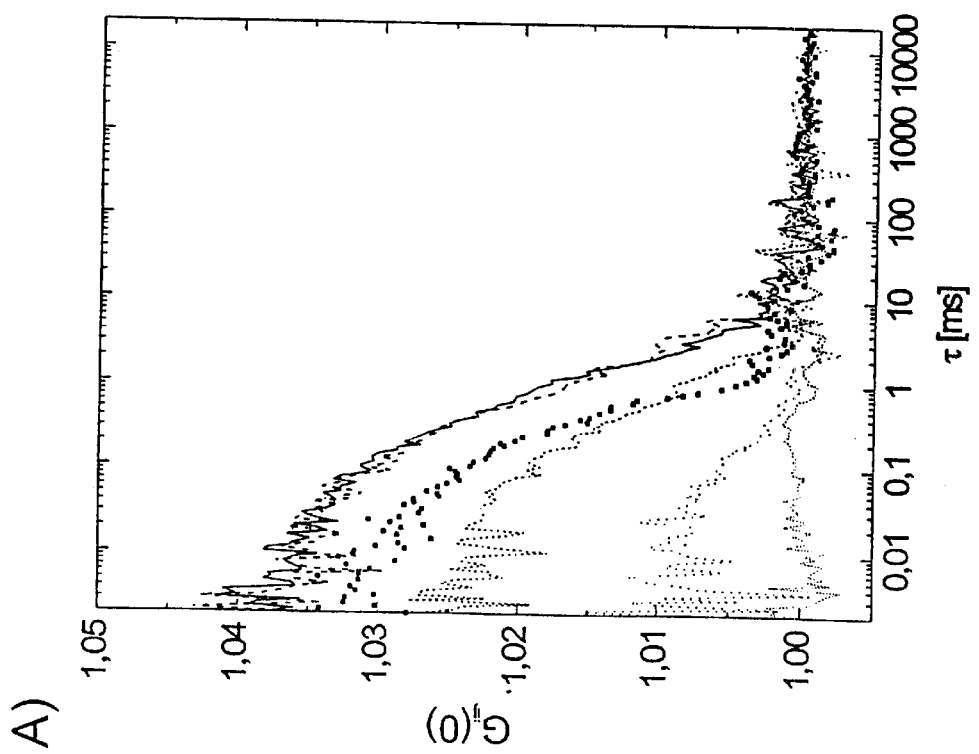

METHOD FOR MEASURING THE ASSOCIATION OF SUBSTRUCTURES OF PATHOLOGICAL PROTEIN DEPOSITIONS

The present invention relates to a method for the diagnostic detection of diseases associated with pathological protein depositions.

A number of diseases is associated with the occurrence of pathological protein depositions. It is often unclear whether the protein depositions are only manifestations of a clinical picture, or whether such protein depositions themselves are the pathogens and thus the cause of the disease. Thus, neurodegenerative diseases are known in which, for example, protein depositions referred to as amyloid plaques can be detected in the brain of afflicted persons. Such diseases include, for example, Alzheimer's disease, bovine spongiform encephalopathy (BSE), Creutzfeldt-Jakob disease (CJD), laughing death syndrome, scrapie, and possibly other diseases which were referred to as "slow virus" diseases in the past. More recently, the BSE disease, in particular, has become a focus of public attention, which is due to the fact, inter alia, that BSE has been connected with the Creutzfeldt-Jakob disease in humans. Today, the mechanisms by which the protein depositions affect the pathological process are still unclear. The relationship, observed by Prusiner, between infectiosity and the concentration of certain proteins which play a role in the pathological process of scrapie, a neurodegenerative disease in sheep, is remarkable. Pathological protein depositions appear not only in diseases of the neuronal system, but are observed in other organs as well, such as in a disease of diabetes type II.

A survey of prion diseases has been published by D. Riesner in "Chemie in unserer Zeit" (1996), p. 66–74. Inter alia, it is set forth therein that a reliable and quick diagnosis is a priority problem of prion research, not only to ensure biological safety, but also to promote the basic research which involves a lot of open questions as to the replication and pathogenesis of prions. Especially for Alzheimer's disease, the pathological picture has been described relatively well. "Senile plaques", which substantially consist of aggregated amyloid-$\beta$ protein, and "paired helical filaments", which are constituted of abnormally altered tau protein, are closely connected with Alzheimer's disease. The present state of the art of the biochemical diagnosis of Alzheimer's disease is the immunological concentration measurement of soluble A$\beta$ peptides (Motter et al., reduction of $\beta$-amyloid peptide$_{1-42}$ in the cerebrospinal fluid of patients with Alzheimer's disease, Ann. Neurol. 38: 643; 1995) or of the soluble tau protein (Vadermeeren et al., Detection of tau proteins in normal and Alzheimer's disease cerebrospinal fluid with a sensitive sandwich enzyme-linked immunosorbent assay, J. Neurochemistry 61: 1828–1834; 1993) in the cerebrospinal fluid. In the U.S. Pat. No. 5,593,846, a method for determining the concentration of soluble amyloid-$\beta$ protein has been described. However, the actual pathological component, the protein depositions themselves, cannot be measured with this method.

After having concentrated cerebrospinal fluid, Townsend found structures therein which can be stained with the long known dye thioflavine S which is specific for protein aggregates (Townsend et al., 1987, Neurochemical Pathology, 6, 213–229).

In the corresponding U.S. Pat. No. 5,486,460, a method for diagnosing Alzheimer's disease is described in which concentrated cerebrospinal fluid is plated on a glass surface and, after having dried, stained with thioflavine S. However, this method is inconvenient in practice. In addition, the staining method with thioflavine S is not unambiguous for pathological protein depositions linked with Alzheimer's disease (see above). The method described did not meet with any further attention in the relevant art, and neither did the corresponding publication.

In U.S. Pat. No. 5,434,050, Maggio describes a method for diagnosing Alzheimer's disease by associating A$\beta$ peptides to A$\beta$ aggregates, which are present as a solid bound structure, e.g., as a brain slice material. However, this diagnostic method can be practiced only post mortem, as in the living patient, it would require a severe surgical intervention for obtaining brain biopsy material.

Therefore, it has long been desired to perform a measurement in body fluids, such as cerebrospinal fluid.

Surprisingly, the above object is achieved by a diagnostic method having the features of claim 1.

FIG. 8 shows a scheme of the screening for active substances.

FIG. 9 shows the cross-correlation function of fluorescence-labeled prion protein (90-231).

Figure 1:
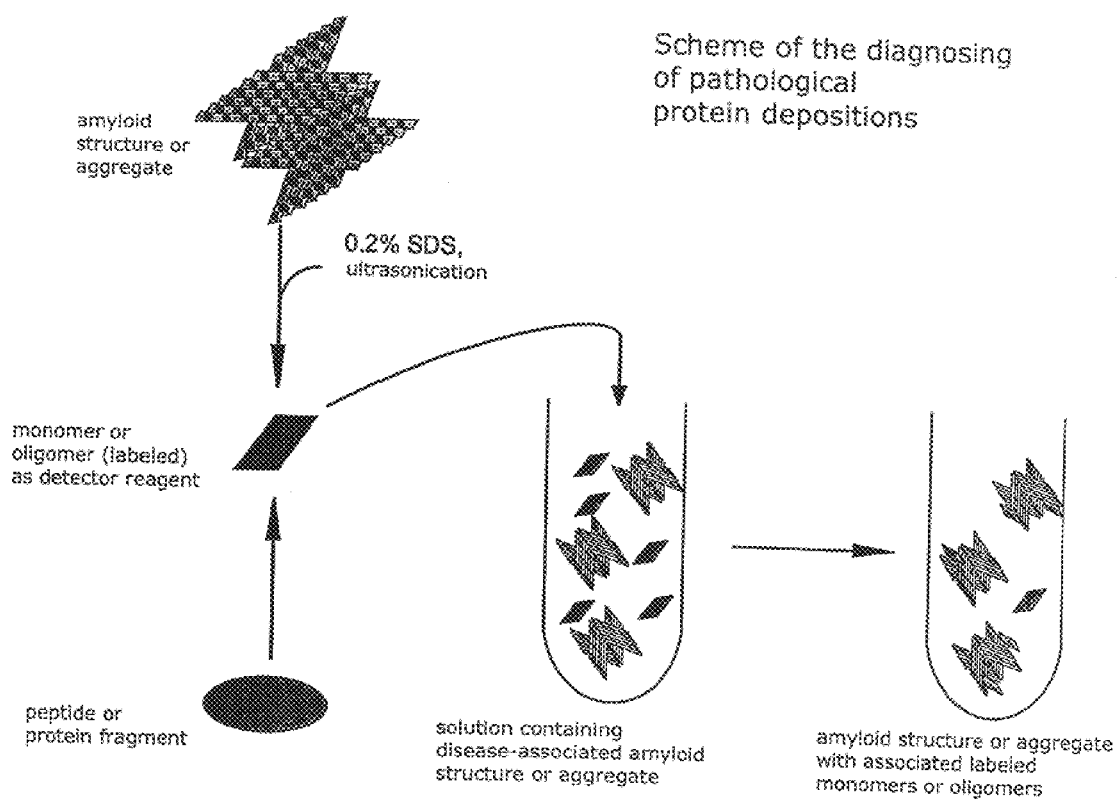
FIG. 1 shows a scheme of the method according to the invention for diagnosing pathological protein depositions.
Figure 2:
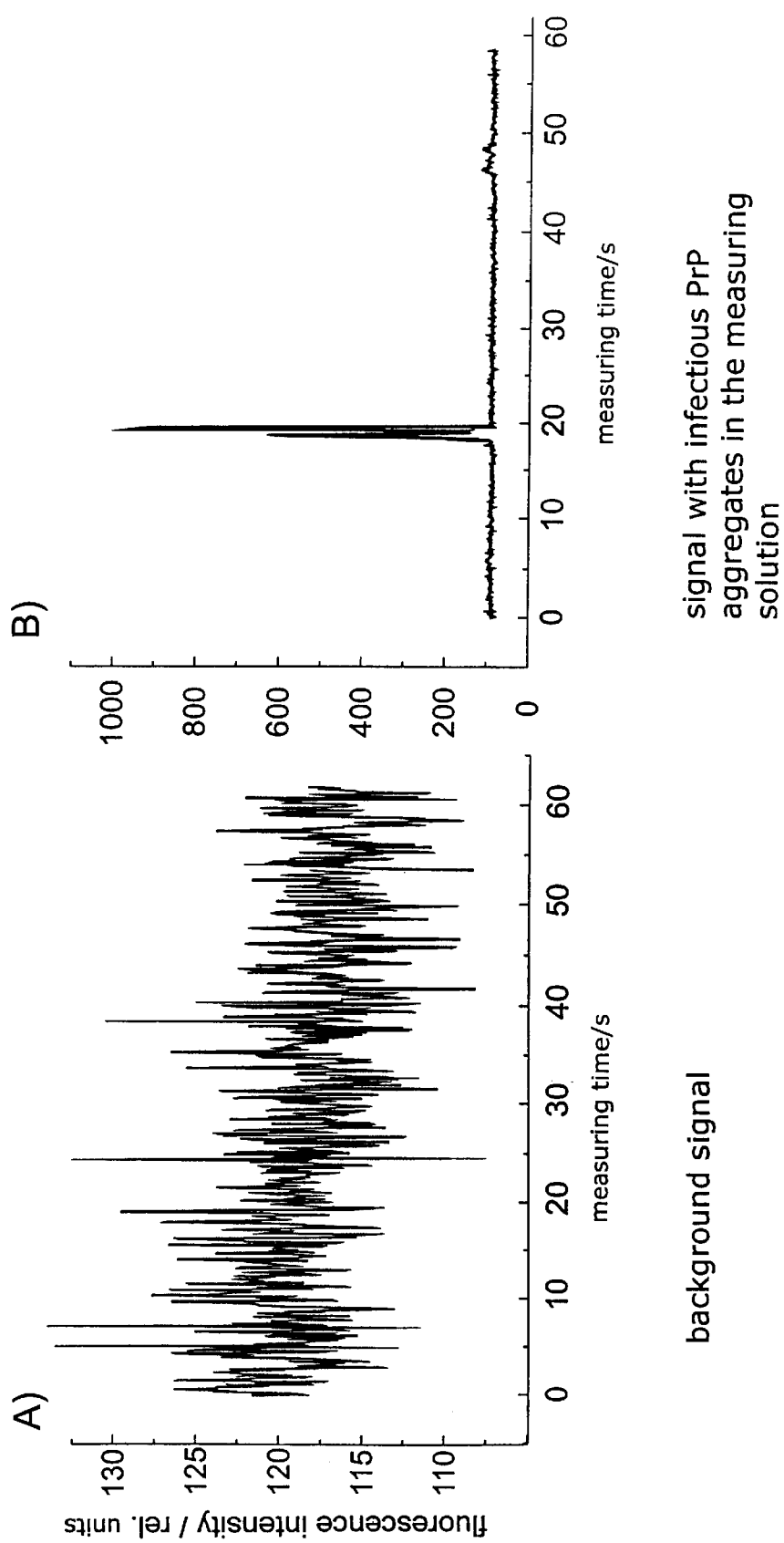
FIG. 2 shows the results of an experiment for the detection of prion-protein aggregates by fluorescence correlation spectroscopy.
Figure 3:
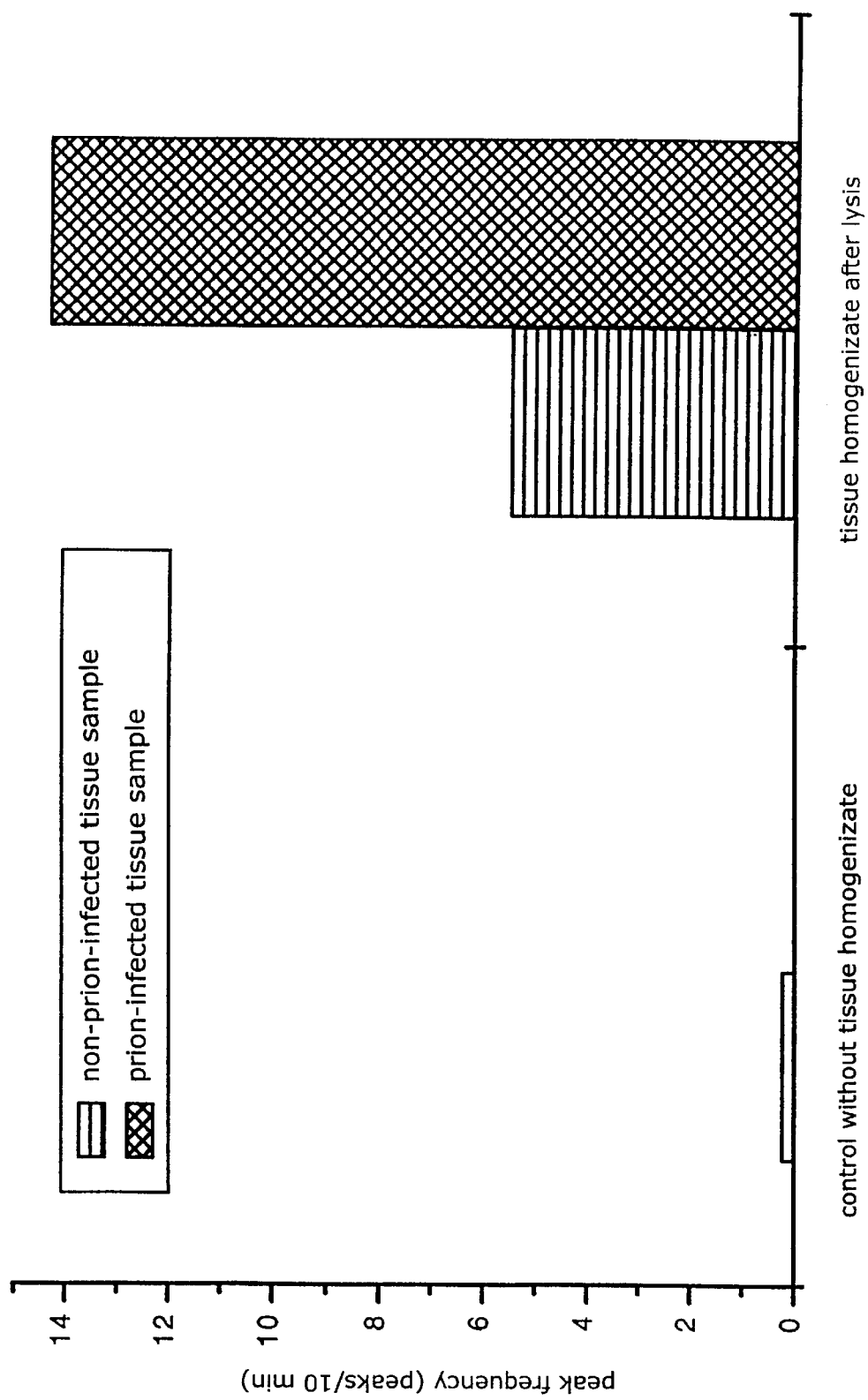
FIG. 3 shows the results of an experiment for the detection of isolated prions from tissue samples by fluorescence-labeled solubilized prion proteins (PrP-Cy2).

The method according to the invention for the diagnostic detection of diseases comprises the measurement of the association of substructures of the pathological protein depositions, structures forming pathological protein depositions, structures corresponding to pathological protein depositions and/or pathological protein depositions as a probe to substructures of the pathological protein depositions, structures forming pathological protein depositions, structures corresponding to pathological protein depositions and/or pathological protein depositions as targets.

The method according to the invention is characterized in that the target is detected in liquid phase wherein, in the case of detecting Alzheimer's disease, the liquid phase is obtained from body fluids or is itself a body fluid. The association of the probe to the target is measured before self-aggregation of the probe predominates.

If the association of the probe to the target recedes into the background before self-aggregation of the probe, a reliable measurement can no longer be ensured. Usually, measuring times in the range of minutes and hours are possible, from which the method appears to be sufficient for use in routine laboratories. The times in which the measurements are performed naturally depend on the respective measuring conditions, but can be established relatively easily in preliminary experiments. As parameters which can influence the measuring time, there may be mentioned, in particular, the concentrations of the targets/of the probe. For example, if the probe concentrations are rather high as compared to the target concentration, self-aggregation of the probes will start sooner than it would be the case if the probes were present in a low concentration or if the probe concentration even was of a similar order of magnitude as the target concentration or lower.

Measuring times of less than one hour, especially less than 30 minutes, are preferred. Such measuring times are advantageous for performing diagnoses in a routine manner.

According to the invention, the probe and/or the target preferably have a detectable property.

Preferably, the substructures of the pathological protein depositions are monomeric or oligomeric units of pathological protein depositions. The substructures may also be homologous, especially structurally homologous, with monomeric or oligomeric units of pathological protein depositions.

The probe may be derived from the same (homologous detection) or a different type (heterologous detection) of pathological protein depositions from that used as the target. Thus, for example, a structure forming pathological protein depositions, a structure corresponding to pathological protein depositions and/or pathological protein depositions themselves derived from a prion disease, such as scrapie or BSE, may be employed as the target while the probe may also be derived, for example, from other structures than those mentioned. Thus, it is possible, for example, to measure the association of substructures (probe) derived from amyloid depositions from BSE to protein depositions connected with Alzheimer's disease.

The substructures employed according to the invention may preferably be obtained by treating pathological protein depositions with physical means, such as ultrasonication, the action of temperature changes, chemical means, such as treatment with solutions of different ionic strengths, treatment with solutions of chaotropic ions, treatment with detergents and/or enzymes, especially proteases. Thus, it is possible, for example, to disrupt amyloid plaques from scrapie-afflicted neuronal tissue into substructures by enzymatic degradation followed by ultrasonication in the presence of detergents; subsequently, these substructures may again form fibrillar structures. The substructures of the pathological protein depositions may also be recombinant proteins, protein fragments or peptides which may have sequence homologies with the corresponding amyloid plaques of various origins and types. Structures corresponding to pathological protein depositions may also be used as probes. Such structures mimic regions of the actual pathological protein depositions and associatively interact with the targets.

Structures forming pathological protein depositions may be used as targets to which the association of probes is measured. This means structures which themselves are not the actual pathological protein depositions, but monomeric or oligomeric units of the pathological protein depositions, or larger aggregates of the substructures of the pathological protein depositions the association of which is to be measured. As an alternative, the pathological protein depositions themselves may also be used.

The probe and/or the target preferably have a detectable property. Said detectable property is either intrinsic to the above mentioned structures or protein depositions, especially to the substructure, or it can be introduced later. Said at least one detectable property is established, in particular, by physical methods, preferably by spectroscopy. As a detectable property of the above mentioned structures or protein depositions, especially the substructure, their size or dimensions may be used, for example. Properties such as the structure, measurable by circular dichroism, optical properties such as luminescence, fluorescence or absorption may also be employed for measuring the association of the probes to the targets. Thus, for example, both the intrinsic fluorescence of structures and the fluorescence of later labeled structures having fluorescent properties can be used.

To increase the specificity or selectivity of the diagnostic detection, other substances which interact with the targets may be used. For example, it is possible to allow substances having an affinity for the targets, for example, antibodies or avidin/biotin, to interact with the targets.

As the methods for measuring said at least one detectable property of the above mentioned structures or associations, there may be preferably employed fluorimetric methods, such as confocal fluorescence spectroscopy, fluorescence correlation spectroscopy (FCS), FCS in combination with cross-correlation, with their respective appropriate evaluation methods. Included herein by reference are DE 44 38 341 and WO-A-96/13744, WO-A-94/16313, and EP-A-96 116 373 and EP-A-97 109 353. Especially the use of FCS cross correlation is of advantage because the specificity of the method can be improved by this method. False positive detections of aggregates in biological media can be suppressed, in particular, by the use of different substructures as probes or the combined use together with other probes for pathological protein depositions, such as specific antibodies.

It may be preferred to recur to a method of "screening" the measuring solution through a confocal volume element moved through the measuring solution in order to increase the sensitivity of detection and to increase the rate of the analyses.

When cross correlation is used, two species having different fluorescence are respectively observed.

The detectable properties are generated, for example, by fluorescence labels which may be low-molecular weight groups, but also high-molecular weight groups. Thus, for example, labeled antibodies which are bound to the targets may label the latter. Then, the binding of probes can be appropriately measured. Different probes may be labeled in different colors, for which cross correlation is then performed. It is also possible to provide the probes with appropriate labels which are either low-molecular weight fluorescent ligands and/or corresponding label conjugates.

According to the invention, the pathological protein depositions are preferably derived from amyloid plaques which accompany neurodegenerative diseases, such as Alzheimer's disease, bovine spongiform encephalopathy (BSE), Creutzfeldt-Jakob disease, scrapie, Huntington's chorea, Parkinson's disease, or from amyloid plaques from organs other than the neuronal system, such as protein depositions associated with diabetes. A suitable source for the pathological protein depositions are organ extracts, preferably brain extracts of afflicted animals. This may be, for example, prion-infected Syrian gold hamsters. The following survey lists diseases which are associated with amyloid phenomena:

| amyloid disease | occurrence | amyloid-forming protein |
| --- | --- | --- |
| Alzheimer's disease | neuronal | amyloid-β protein |
| transmissible spongiform encephalopathies | neuronal | prion protein |
| Huntington's chorea* | neuronal | huntingtin* |
| Parkinson's disease | neuronal | synuclein* |
| hereditary cerebral amyloid angiopathy | neuronal | cystatin C |
| primary systemic amyloidosis (AL amyloidosis) | systemic | immunoglobulin |
| reactive systemic amyloidosis (AA amyloidosis) | systemic | lipoproteins |
| familial amyloid polyneuropathy | systemic | transthyretin |
| type II diabetes | pancreas | islet amyloid polypeptide |
| injection-localized amyloidosis | | insulin |
| medullary carcinoma of the thyroid gland | thyroid gland | calcitonin |
| beta-2 microglobulin amyloidosis | skeleton muscles | beta-2 microglobulin |
| hereditary non-neuropathic amyloidosis | systemic | lysozyme |
| Finnish hereditary systemic amyloidosis | systemic | gelsolin |

(*modified from Sipe, 1992 Annual Reviews in Biochemistry 61; 947–975)

The substructures of the pathological protein depositions may also be recombinant proteins, protein fragments or peptides which have sequence homologies with amyloid plaques. Thus, for example, conservative amino acid substitutions in highly conserved regions can be as follows: any isoleucine, valine and leucine amino acid may be exchanged for any other of these amino acids, aspartate may be exchanged for glutamate or vice versa, glutamine for asparagine or vice versa, serine for threonine or vice versa. Conservative amino acid substitutions in less highly conserved regions can be as follows: any of the amino acids isoleucine, valine and leucine may be exchanged for any other of these amino acids, aspartate for glutamate or vice versa, glutamine for asparagine or vice versa, serine for threonine or vice versa, glycine for alanine or vice versa, alanine for valine or vice versa, methionine for any of the amino acids leucine, isoleucine or valine, lysine for arginine or vice versa, any of the amino acids aspartate or glutamate for any of the amino acids arginine or lysine, histidine for any of the amino acids arginine or lysine, glutamine for glutamate or vice versa, and asparagine for aspartate or vice versa.

As the source for material which is subjected to a diagnostic examination by the method according to the invention, there may be used, in particular, body fluids, such as cerebrospinal fluid, blood, lymph, urine or secretions such as sputum. From the mentioned body fluids or secretions, samples are taken and contacted with probes and incubated for measuring the association of structures forming pathological protein depositions, structures corresponding to pathological protein depositions and/or pathological protein depositions which could be contained in these samples. The presence of the pathological protein depositions which are indicative of a related disease will then give a positive diagnostic signal, mediated by the association of the added probes. Body fluids are advantageous over tissues because they can be subjected to direct incubation whereas tissues must be first lysed as a rule. This may be done, for example, by mechanical or chemical treatment or combinations thereof.

The parameters established from the detectable properties of the mentioned structures and depositions, especially substructures, may be, in particular, translational diffusion rates, rotational diffusion rates, lifetimes of excited states, polarization of radiation, energy transfer, quantum yield, number or concentration of particles, intensity differences. If the translational diffusion rate is established, it may be desirable for slowly diffusing associates to detect them by multiple detection using a scanning process.

The load on the patient from the lumbar punction for obtaining cerebrospinal fluid is low. A significant increase in sensitivity can be achieved when a nucleated polymerization process is included as theoretically described by Jarret and Lansbury (Cell 73, 1055–1058, 1993) for amyloid diseases. In this model, the aggregation of amyloid depositions is classified into two kinetic reactions. In the self-aggregation kinetics of amyloid proteins into oligomeric subunits, the equilibrium is clearly on the side of the educts. Aggregates only form after an extended reaction time. A nucleation-dependent polymerization ensues in which amyloid proteins associate to the aggregates already present. Here, the equilibrium is clearly on the side of the products. Association occurs without a time delay. This time window between the two kinetic reactions should be useful for the detection of natural protein depositions. After adding a probe which can support a polymerization process, in the case of the presence of pathological protein depositions serving as nuclei, a clearly accelerated inclusion of the probe into such protein deposition should occur as compared to the formation of the aggregates formed by the slower self-aggregation of the probe which, however, may not be distinguishable from the former aggregates.

Especially the combination of nucleated association of a multitude of labeled probes to pathological protein depositions serving as the nuclei, with the extremely sensitive detection method by confocal optics yields a correspondingly large amplification of the measuring signal. Thus, in the cerebrospinal fluid obtained by lumbal punction (Neumeister et al., Klinikleit-faden Labordiagnostik, Fischer-Verlag 1998), individual molecules of the pathological protein depositions could be unambiguously detected.

A screening method for detecting active substances for the treatment of diseases associated with pathological protein depositions, which is analogous with the method according to the invention, is based on the fact that the association of substructures of the pathological protein depositions, structures forming pathological protein depositions, structures corresponding to pathological protein depositions and/or pathological protein depositions to substructures of the pathological protein depositions, structures forming pathological protein depositions, structures corresponding to pathological protein depositions as targets is measured in the presence of suspected active substances. As an alternative, association of substructures of pathological protein depositions, structures forming pathological protein depositions, structures corresponding to pathological protein depositions and/or pathological protein depositions to substructures of the pathological protein depositions, structures forming pathological protein depositions, structures corresponding to pathological protein depositions as targets is first performed, and then the reversal of the association under the action of suspected active substances is observed. Then, those compounds are identified as active substances which are capable of causing a reversal of the association in a significant way. A third alternative is the measurement of the dissociation of protein depositions themselves under the action of suspected active substances.

The method according to the invention is further illustrated by the following Examples.

The scheme shown in FIG. 1 shows the experimental procedure for the following Examples 1 to 6, 8 to 10.

Experiments 1 to 3 and 5 were performed with solubilized prion proteins while experiments 7 to 10 relate to recombinant prion protein (90-231).

The preparation of soluble (solubilized) prion proteins (PrP) was effected by ultrasonication in 10 mM sodium phosphate, pH 7.2, 0.2% SDS, of prion aggregates isolated from infectious brain tissue of the Syrian gold hamster (Riesner, D.; Kellings, K.; Post, K.; Wille, H.; Serban, H.; Groth, D.; Baldwin, M. A.; and Prusiner, S. B.; 1996, Journal of Virology, Vol. 70, No. 3, pages 1714–1722). Depending on the energy of ultrasonication, a monomeric to oligomeric PrP fraction is formed which was fluorescence-labeled for the Examples described in the following (1 to 3, 5) (Pitschke, M.; Post, K.; and Riesner, D.; 1997, Progress in Colloid & Polymer Science, Vol. 107, pages 72–76). For fluorescence labeling, the dye Cy2 (Amersham) was used.

Soluble Aβ(1-42) could be stabilized in 10 mM Na phosphate buffer, pH 7.0, with 0.2% SDS (Examples 4, 6). The dye Cy2 (Amersham) was also used for the fluorescence labeling of Aβ.

For association measurements, the soluble, monomeric to oligomeric fluorescence-labeled proteins or peptides were incubated with amyloid aggregates (infectious prion particles: Examples 1 to 3; Aβ: Examples 4 to 5) with diluting the SDS to 0.2% SDS, and the fluorescence signal was detected by fluorescence correlation spectroscopy.

EXAMPLE 1

Detection of Prion-Protein Aggregates by Fluorescence Correlation Spectroscopy (FCS)

Detection of infectious prion particles (PrP) by FCS through the association of fluorescence-labeled solubilized PrP.

Material solubilized PrP-Cy2, about 25 ng/μl in 10 mM Na phosphate buffer, pH 7.0, 0.2% SDS; →(solution 1)

prion particles (about 200 ng/μl) in 10 mM Na phosphate buffer, pH 7.0; →(solution 2)

Performance

Two batches were prepared:

| | |
|---|---|
| A) 1 μl of solution 1 (1:10)<br>19 μl of Na phosphate buffer, pH 7.0 | B) 1 μl of solution 1 (1:10)<br>17 μl of Na phosphate buffer, pH 7.0<br>2 μl of solution 2 (1:100) |

Each of the two charges was mixed, incubated for 1 minute, charged into a sample chamber and measured by FCS.

FIG. 2 shows the result of a measurement of fluorescence intensity (in relative units; RU) over a period of 60 seconds. In FIG. 2*a*, the fluctuation signal of the solubilized PrP-Cy2 is seen; it has a signal intensity between 110 and 130 RU. Evaluation of the signal using autocorrelation yields a diffusion time of about 250 μs which is typically that of the monomeric protein. In FIG. 2*b*, a signal peak having a fluorescence intensity of about 950 RU is additionally seen; it is caused by the slow diffusion of a larger aggregate to which the previously solubilized fluorescence-labeled PrP-Cy2 is associated. Since this is a single event, determination of the diffusion time or molecular weight by autocorrelation is not possible. An unambiguous signal detection and assignment to individual aggregates is successfully achieved, however, through the occurrence of isolated peaks with a drastic increase in fluorescence intensity.

EXAMPLE 2

Homologous Detection of Isolated Prions from Tissue Samples Using Fluorescence-labeled Solubilized Prion Proteins (PrP-Cy2)

Detection of infectious aggregates of the prion proteins (PrP rods) in brain extracts after labeling with fluorescence-labeled solubilized prion proteins (PrP-Cy2) using FCS.

Material solubilized PrP-Cy2, about 25 ng/μl in 10 mM Na phosphate buffer, pH 7.0, 0.2% SDS; →(solution 1)

brain extract from non-infected (solution 2) and prion-infected Syrian gold hamsters (solution 3)

Performance

Two batches were prepared:

| | |
|---|---|
| A) 1 μl of solution 1 (1:10)<br>17 μl of Na phosphate buffer, pH 7.0<br>2 μl of solution 2 (1:10) | B) 1 μl of solution 1 (1:10)<br>17 μl of Na phosphate buffer, pH 7.0<br>2 μl of solution 3 (1:10) |

Each of the two charges was mixed, incubated for 1 minute, charged into a sample chamber and measured by FCS.

As a control, solubilized PrP-Cy2 without addition of brain extract was measured in the same concentration.

In FIG. 3, the peak frequency for the individual charges is plotted as a graphical representation. The number of the peaks caused by the diffusion of high-molecular weight aggregates through the confocal volume element (see Example 1) was detected. It can be seen that the prion-infected tissue sample has a significantly higher peak frequency as compared to the sample with non-infected brain extract.

Detection of infectious material through the association of solubilized PrP-Cy2 to existing prions is possible with this experimental design even if the peak frequency shows a background in examinations of non-infected tissue samples.

EXAMPLE 3

Sensitivity of the Homologous Association of Fluorescence-labeled Solubilized Prion Proteins (PrP-Cy2) and of Prion-protein Aggregates Isolated from Tissue Samples The sensitivity of the homologous association of PrP-Cy2 to prions isolated from infectious brain tissue is analyzed by FCS.

Material solubilized PrP-Cy2, about 25 ng/μl in 10 mM Na phosphate buffer, pH 7.0, 0.2% SDS; →(solution 1)

PrP rods (about 200 ng/μl) in 10 mM Na phosphate buffer, pH 7.0; →(solution 2)

Performance

Two series of experiments were prepared:

| | |
|---|---|
| A) 1 μl of solution 1 (1:10)<br>17 μl of Na phosphate buffer, pH 7.0<br>2 μl of solution 2 (1:x; PrP quantity see FIG. 4) | B) 1 μl of solution 1 (1:10)<br>17 μl of Na phosphate buffer, pH 7.0; 0.2% SDS<br>2 μl of solution 2 (1:x; PrP quantity see FIG. 4) |

The quantity of PrP rods in the experimental charge was reduced stepwise down to the detection limit. The measurement in 0.2% SDS served as a control.

Every batch was mixed, incubated for 1 minute, charged into a sample chamber and measured by FCS.

Figure 4:
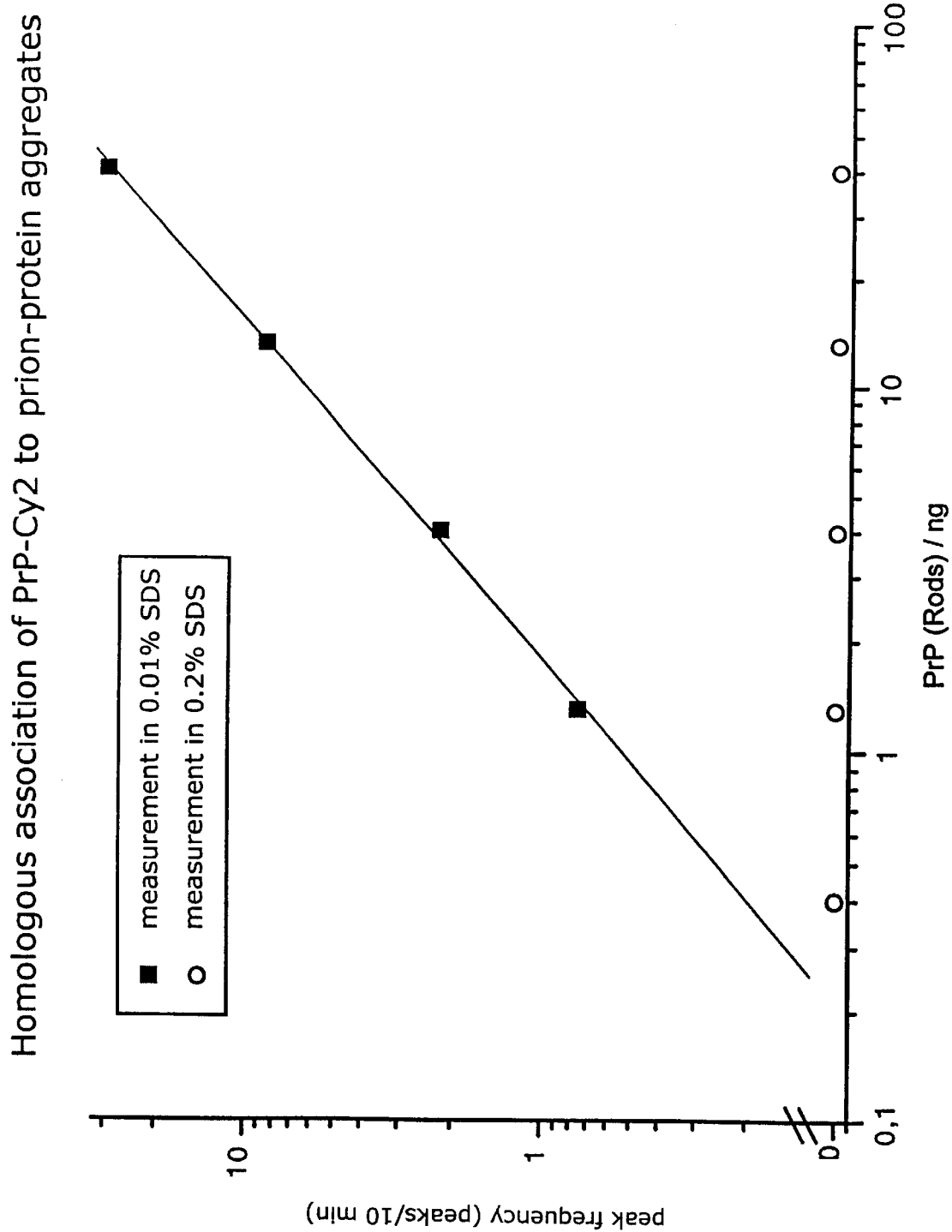
FIG. 4 shows the sensitivity of the homologous association of fluorescence-labeled solubilized prion proteins (PrP-Cy2) to prion-protein aggregates from tissue samples and the influence of SDS concentration.

The peak frequency expressed in peaks per 10 min of measuring time was plotted against the PrP quantity in the experimental charge in FIG. 4. Over the measured concentration range of 40 ng to 400 pg, a direct linear dependence of the peak frequency can be seen. Thus, evaluation of the number of peaks enables a direct quantification of the prion concentration in the sample to be measured. In 0.2% SDS, incorporation in existing PrP structures is not possible.

EXAMPLE 4

Homologous Detection of Peptide Aggregates, which Represent the Majority of Amyloid Depositions in Alzheimer's Disease, with Fluorescence-labeled Soluble Aβ(1-42) Peptide Detection of aggregates from Alzheimer's disease with fluorescence-labeled soluble Aβ(1-42) using FCS, to answer the question of whether the detection method employed in Examples 1 to 3 can be transferred to other diseases involving pathological protein depositions and is thus suitable for detection of any amyloid structure.

Material
    soluble Aβ peptide 1-42, fluorescence-labeled with Cy2, 100 ng/βl in 10 mM Na phosphate buffer, pH 7.0, 0.2% SDS; →(solution 1)
    Aβ amyloid fibrils (90 ng/µl) in 10 mM Na phosphate buffer, pH 7.0; →(solution 2)

Performance
    Two batches were prepared:

| A) 1 µl of solution 1 (1:10)<br>10 µl of solution 2<br>9 µl of Na phosphate buffer, pH 7.0 | B) 1 µl of solution 1 (1:10)<br>10 µl of solution 2<br>9 µl of Na phosphate buffer, 0.2% SDS, pH 7.0 |
|---|---|

Each of the two charges was mixed, incubated for 1 minute, charged into a sample chamber and measured by FCS.

As a control, soluble Aβ(1-42)-Cy2 was measured in the same concentration.

Figure 5:
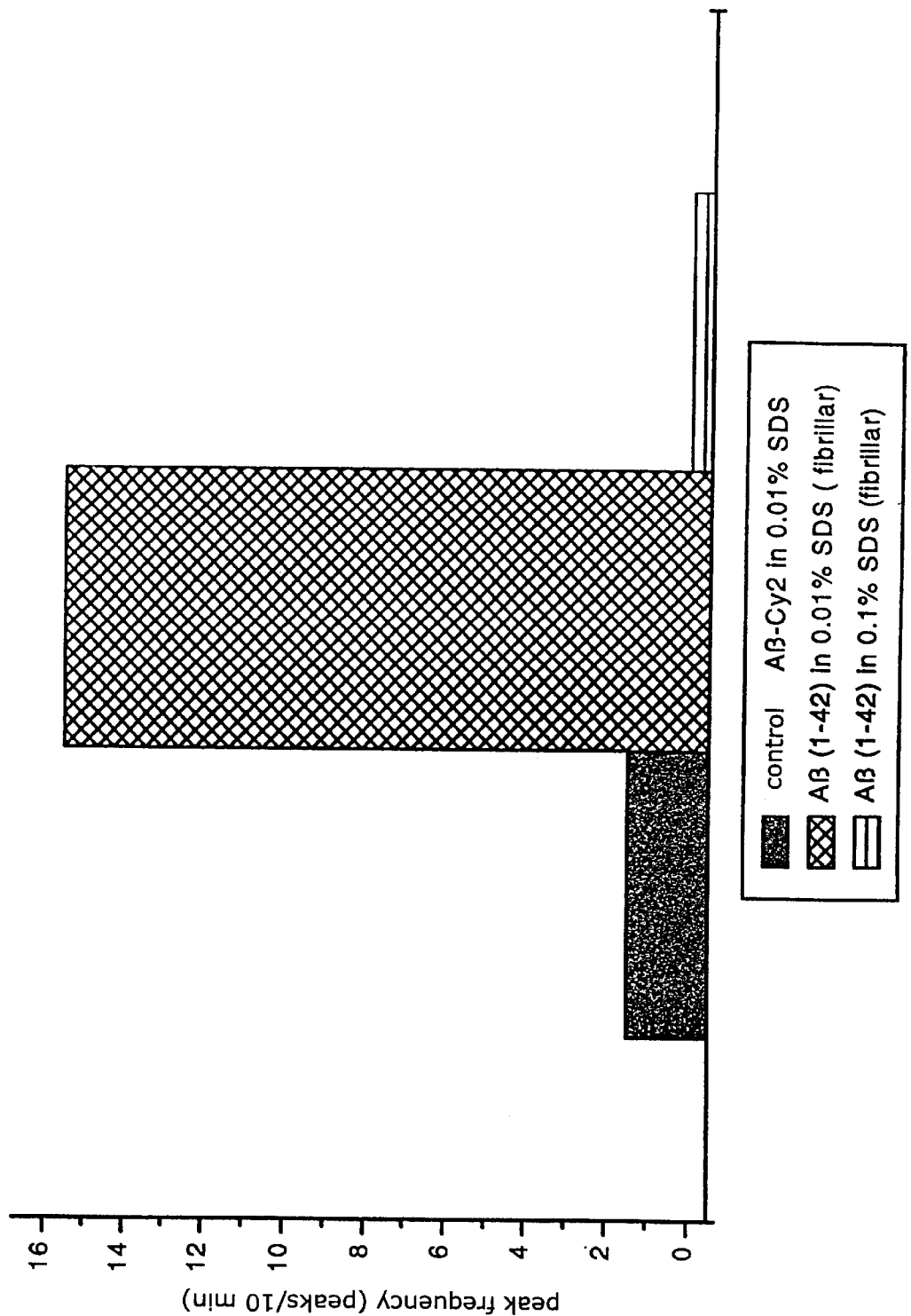
FIG. 5 shows the homologous detection of peptide aggregates, which represent the majority of amyloid depositions in Alzheimer's disease, with fluorescence-labeled soluble A$\beta$(1-42) peptide.

In FIG. 5, the results of the experiment are summarized graphically. The evaluation of peak frequency (cf. 1–3) shows that with incubation in 0.01% SDS, labeling of Aβ fibrils (SDS concentration identical with that used for PrP aggregates), which represent the major components of amyloid depositions in Alzheimer's disease, is possible by this method. Incorporation of Aβ-Cy2(1-42) in the presence of an increased SDS concentration (0.1%) is not possible. The labeling of Aβ which is present in a soluble (rather than fibrillar) structure is not possible either. The experiment shows that the detection of amyloid depositions accompanying Alzheimer's disease is possible.

EXAMPLE 5

Heterologous Detection of Peptide Aggregates, which Represent the Majority of Amyloid Depositions in Alzheimer's Disease, with Fluorescence-labeled Solubilized Prion Proteins (PrP-Cy2)

Detection of aggregates from Alzheimer's disease with fluorescence-labeled soluble PrP-Cy2 using FCS, to answer the question of whether a heterologous labeling with a fluorescence-labeled soluble probe not identical with the sample to which association is to take place is possible.

Material
    solubilized PrP-Cy2, about 25 ng/µl in 10 mM Na phosphate buffer, pH 7.0, 0.2% SDS; →(solution 1)
    Aβ(1-42) amyloid fibrils (90 ng/µl) in 10 mM Na phosphate buffer, pH 7.0; →(solution 2)
    Aβ(1-42), non-fibrillar (90 ng/µl) in 10 mM Na phosphate buffer, pH 7.0, 0.2% SDS; →(solution 3)
    Aβ(1-40) amyloid fibrils (90 ng/µl) in 10 mM Na phosphate buffer, pH 7.0; →(solution 4)
    Aβ(1-40), non-fibrillar (90 ng/µl) in 10 mM Na phosphate buffer, pH 7.0, 0.2% SDS; →(solution 5)

Performance
    The following batches were prepared:

Aβ peptide (1–42):

| A) 1 µl of solution 1 (1:10)<br>2.5 µl of solution 2<br>16.5 µl of Na phosphate buffer, pH 7.0<br>C) 1 µl of solution 1 (1:10)<br>2.5 µl of solution 2<br>16.5 µl of Na phosphate buffer, pH 7.0, 0.2% SDS | B) 1 µl of solution 1 (1:10)<br>2.5 µl of solution 3<br>16.5 µl of Na phosphate buffer, pH 7.0 |
|---|---|

Aβ peptide (1–40):

| A) 1 µl of solution 1 (1:10)<br>2.5 µl of solution 4<br>16.5 µl of Na phosphate buffer, pH 7.0<br>C) 1 µl of solution 1 (1:10)<br>2.5 µl of solution 4<br>16.5 µl of Na phosphate buffer, pH 7.0, 0.2% SDS | B) 1 µl of solution 1 (1:10)<br>2.5 µl of solution 5<br>16.5 µl of Na phosphate buffer, pH 7.0 |
|---|---|

Every batch was mixed, incubated for 1 minute, charged into a sample chamber and measured by FCS.

As a control, soluble PrP-Cy2 was measured in the same concentration with 0.01% SDS.

Figure 6:
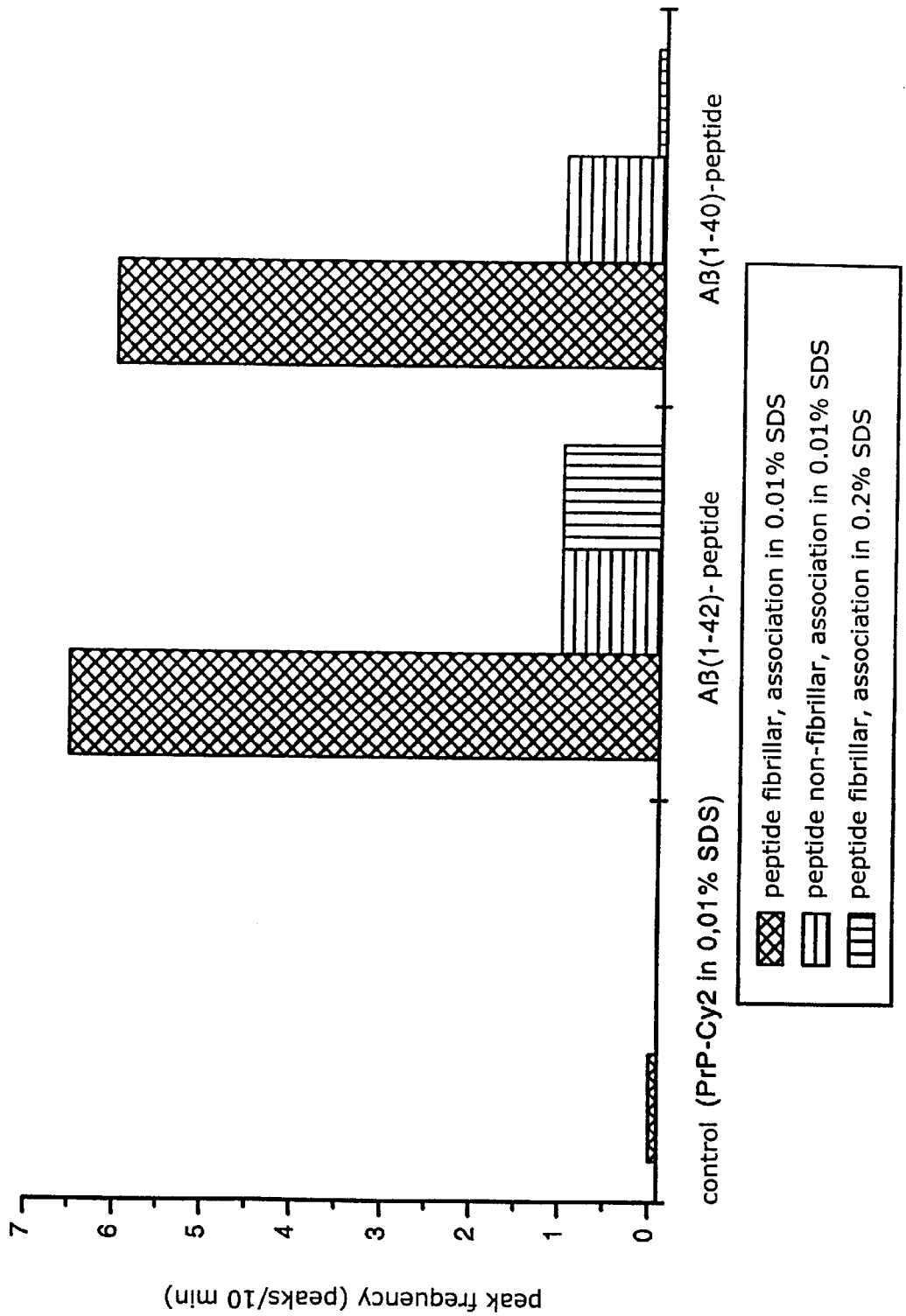
FIG. 6 shows the results of an experiment for the heterologous detection of peptide aggregates, which represent the majority of amyloid depositions in Alzheimer's disease, with fluorescence-labeled solubilized prion protein (PrP-Cy2).

The peak frequency (cf. Example 2) was measured for each of the above mentioned batches (FIG. 6). It is found that both Aβ(1-42) and Aβ(1-40) can be distinctly labeled with PrP-Cy2 if they are present in a fibrillar structure and if the labeling reaction takes place at 0.01% SDS. When association is effected to non-fibrillar structures or the SDS concentration is increased, only a low background signal can be seen.

This result shows that the labeling of amyloid protein aggregates does not forcibly require that the soluble fluorescence-labeled protein employed for labeling be identical with the protein forming the aggregate.

EXAMPLE 6

Detection of Aggregates in the Cerebrospinal Fluid of Patients Suffering from Alzheimer's Disease Specific detection of aggregates associated with Alzheimer's disease. Thus, cerebrospinal fluid (spinal fluid) is used as a sample in which a specific distinction can be made between patients suffering from Alzheimer's disease and a healthy control group.

Figure 7:
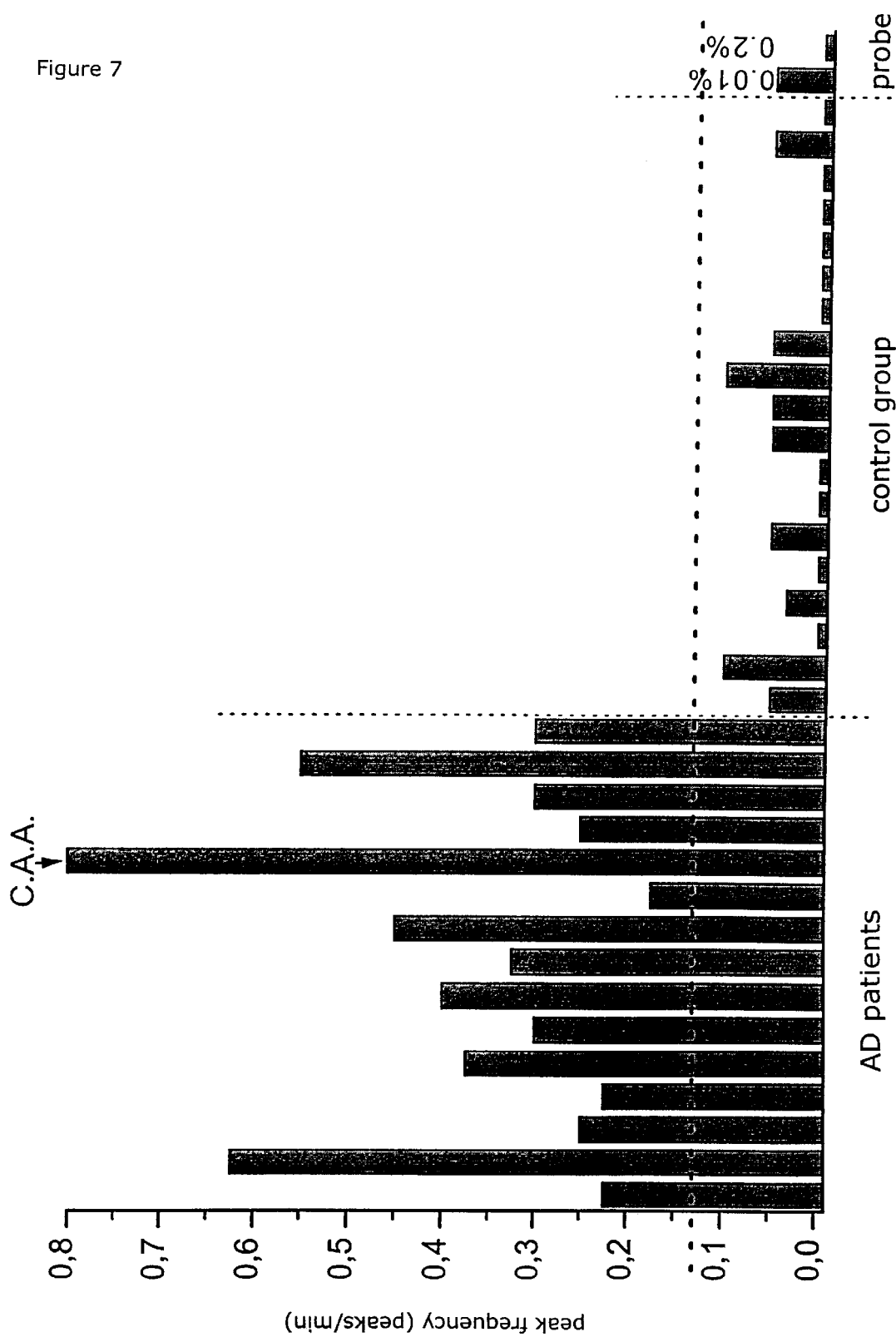
FIG. 7 shows the results of an experiment for the specific detection of aggregates in the cerebrospinal fluid of patients for whom Alzheimer's disease has been diagnosed.

Material
    soluble Aβ peptide 1-42, fluorescence-labeled with Cy2, 100 ng/µl in 10 mM Na phosphate buffer, pH 7.0, 0.2% SDS; →(solution 1)
    cerebrospinal fluid from afflicted patients and control from non-afflicted subjects Performance
    The following batches were prepared:
    2 µl of solution 1 (1:10)
    18 µl of cerebrospinal fluid from patients Without further treatment or concentration, the cerebrospinal fluid samples were directly incubated with fluorescence-labeled Aβ(1-42)-Cy2 (0.1 ng/μl) at 0.02% SDS and immediately measured by FCS for 20 min (FIG. 7). The detected aggregates in cerebrospinal fluid samples from patients afflicted with Alzheimer's dementia (AD) as judged by psychiatric diagnostic criteria and those from non-afflicted control subjects were compared. It is found that all patients afflicted with Alzheimer's dementia have a significantly higher signal intensity in the cerebrospinal fluid as compared to the corresponding control group which had a similar age structure. The patient designated as CAA has the highest signal intensity of all patients subjected to diagnosis. This patient is afflicted with congophile angiopathy, a special form of Alzheimer's disease in which deposition of amyloid-β peptides occurs in the capillaries of the cerebral vessels, the migration of which is thereby gradually destroyed. In this disease, the most massive transgression of Aβ aggregates into the cerebrospinal fluid seems to take place, which results in the large increase of signal intensity. The measuring results of the control group show that aggregates are detected here as well in isolated cases. This result is also shown by the probe alone (Aβ(1-42)-Cy2); it is due to self-aggregation effects occurring during the 20 minutes' measuring time or due to existing Aβ aggregates. The measuring results of the probe were achieved in 0.01% or 0.2% SDS.

EXAMPLE 7
Coaggregation of Two Fluorescence-labeled rPrP Probes to rPrP (90-231)

Recombinant prion protein (90-231) (referred to as rPrP hereinafter) which is homologous with the protease-resistant portion of hamster PrP was labeled with amino-reactive fluorescence dyes of the excitation wavelengths 488 nm (Oregon Green, Molecular Probes) and 633 nm (Cy5, Amersham). The protein concentrations and labeling ratio were determined by absorption measurements at 280 nm, 496 nm and 650 nm. The labeling efficiency was 10% (rPrP-Cy5) and 4% (rPrP-OrG) for equimolar addition of the amino-reactive fluorescence dye.

Aggregation experiments: Equimolar amounts of the two labeled rPrP probes were mixed with a 25 fold excess of unlabeled rPrP, the buffer containing 0.2% SDS. The aggregation process was started by diluting to an SDS concentration of 0.01% and an rPrP total concentration of 50 nM.

The aggregation process was followed by repeatedly recording autocorrelation and cross-correlation curves in two-color cross correlation FCS equipment (ConfoCor prototype, Zeiss). The correlation curves were shaped by a three-dimensional diffusion model wherein a diffusion parameter τrg was used for the cross-correlation curves. Fitting was performed using a model for spherical molecules.

Reduction of the SDS concentration causes a rapid increase of the cross-correlation amplitude which is proportional to the concentration of the particles into which both red and green labeled PrP were incorporated. In the presence of 0.2% SDS, a cross-correlation product could not be detected. In a few minutes, the oligomer concentration rises up to a plateau and then slowly decreases through the formation of higher aggregates.

FIG. 9 (left) shows the cross-correlation function of fluorescence-labeled rPrP(90-231), c(rPrP)=50 nM, c(rPrP-Cy5), c(rPrP-OrG)=2 nM in PBS, 25° C.+0.01% SDS. The curves have the following meanings: a) smaller dots: 1 min incubation time; b) short dashes: 6 min; c) larger dots: 20 min; d) dashed line: 30 min; e) solid line: 130 min; f) small dots: reference sample, 0.2% SDS.

FIG. 9 (right) shows the plot of the cross-correlation amplitude in the course of aggregation (squares). The formation of particles which have incorporated both red and green fluorophores can be described by a second order reaction: $A_i + B_j \rightarrow AB_{ij}$, $k=5\cdot10^6 M^{-1}$.

EXAMPLE 8
Association of rPrP Probes to Existing rPrP Aggregates

Preaggregated rPrP in concentrations of from 0.2 to 20 ng/μl was added to the aggregation batch of Example 7. The rPrP aggregates were produced by incubation of rPrP at an SDS concentration of 0.01% for 1 h at 25° C. (c(rPrP)=100 ng/ml). The association process was followed by the consecutive recording of autocorrelation and cross-correlation curves.

The association of labeled rPrP to the aggregates could be observed within a time in the range of a few minutes. This process was characterized by the occurrence of large fluorescence peaks in the raw signal. The cross-correlation curves were dominated by a component having a high diffusion time (>5 ms).

EXAMPLE 9
Recognition of rPrP Aggregates by the Cross-Correlation of Two Probes: Monoclonal Antibody (mAB)+rPrP For the specific recognition of prion protein, various monoclonal antibodies are available which are distinguished by their specificity and binding strength. Particularly suitable for the recognition of pathogenic PrP in samples of CJD patients is an antibody developed by B. Oesch (Korth et al., Nature, Nov. 6, 1997, 390 (6655): 74–7) which specifically binds the pathogenic form of the prion protein. The combination of specific antibody binding with the coaggregation of PrP probes offers an increased specificity as compared to the single labeling of the pathogenic aggregates.

The monoclonal antibody IgM 15b3 was labeled with a fluorescence dye at its amino functions by analogy with the PrP probes. The labeled antibody was employed in a final concentration of 20 nM. For the mixed use of rPrP and antibody probes, it is desirable that the binding conditions be suitable for both probes. At an SDS concentration of 0.01%, both coaggregation of the rPrP probe and antibody binding can be observed. Entry of a labeled aggregate into the focus produces a fluorescence peak. At an appropriate size, the peak signal dominates the cross-correlation curve.

Figure 10:
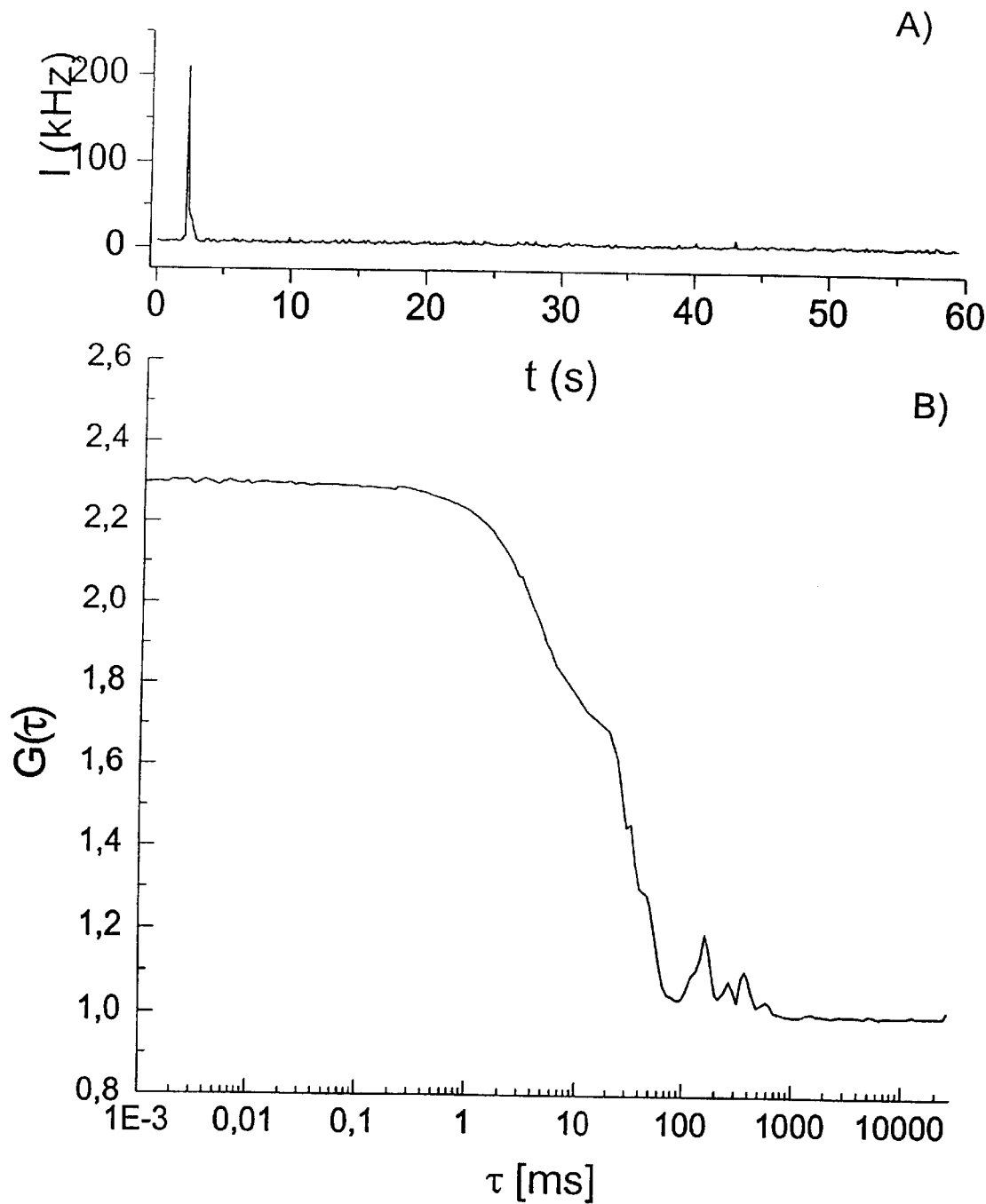
FIG. 10 shows the association of a probe of recombinant prion protein and a monoclonal antibody to a prion-protein aggregate.

FIG. 10 shows the association of the rPrP probe and mAB to an rPrP aggregate. Top: sweep of the cross-correlation fluorescence signal. Bottom: two-color cross-correlation curve. The course of the curve is dominated by the large aggregate at the beginning of the sweep. The concentrations are c(rPrP)=50 nM, c(rPrP-Cy2)=2 nM, c(mAB-Cy5)=20 nM.

EXAMPLE 10
Peak Analysis of the Fluorescence Raw Data

The association of many probe molecules to a protein target generates highly labeled aggregates (>10 incorporated probes) which protrude before the background signal of the free probe by at least a factor of two. The amount of aggregates present in the sample can be determined by the number of peaks. Thus, with measuring times of 15 min, aggregates in concentrations of down to femtomolar can be detected.

One application is the detection of PrP aggregates in the cerebrospinal fluid of CJD patients. Three CJD-negative and three CJD-positive cerebrospinal fluid samples were examined. A differentiation between CJD-positive and CJD-negative samples could be made by the number of events with high fluorescence bursts.

Experimental conditions: Cy2-labeled rPrP probe was added to a cerebrospinal fluid sample in the presence of 0.02% SDS so that the probe concentration was 10 nM. The measurement was effected at 22° C. for 15 min.

Data acquisition: The samples were measured in a ConfoCor FCS design. Excitation was effected at a wavelength of 488 nm ($Ar^+$ laser) with a power density of $5 \cdot 10^4$ W/cm². The emitted fluorescence light was focused by a microscope objective (40×/1.2 NA, Zeiss) and confocally imaged onto an avalanche photodiode. The latter acts as a photon counter which yields one signal pulse for each photon. The signal pulses were transmitted through a signal divider and evaluated in parallel on a hardware correlator card and recorded on a scaler card with a channel width of 250 µs. The total measuring time was 15 min which corresponds to a total of 3.6 million channels.

Data evaluation: The evaluation was performed according to the number and height of the fluorescence peaks. A distribution of the number of photons per channel is shown in a histogram.

Figure 11:
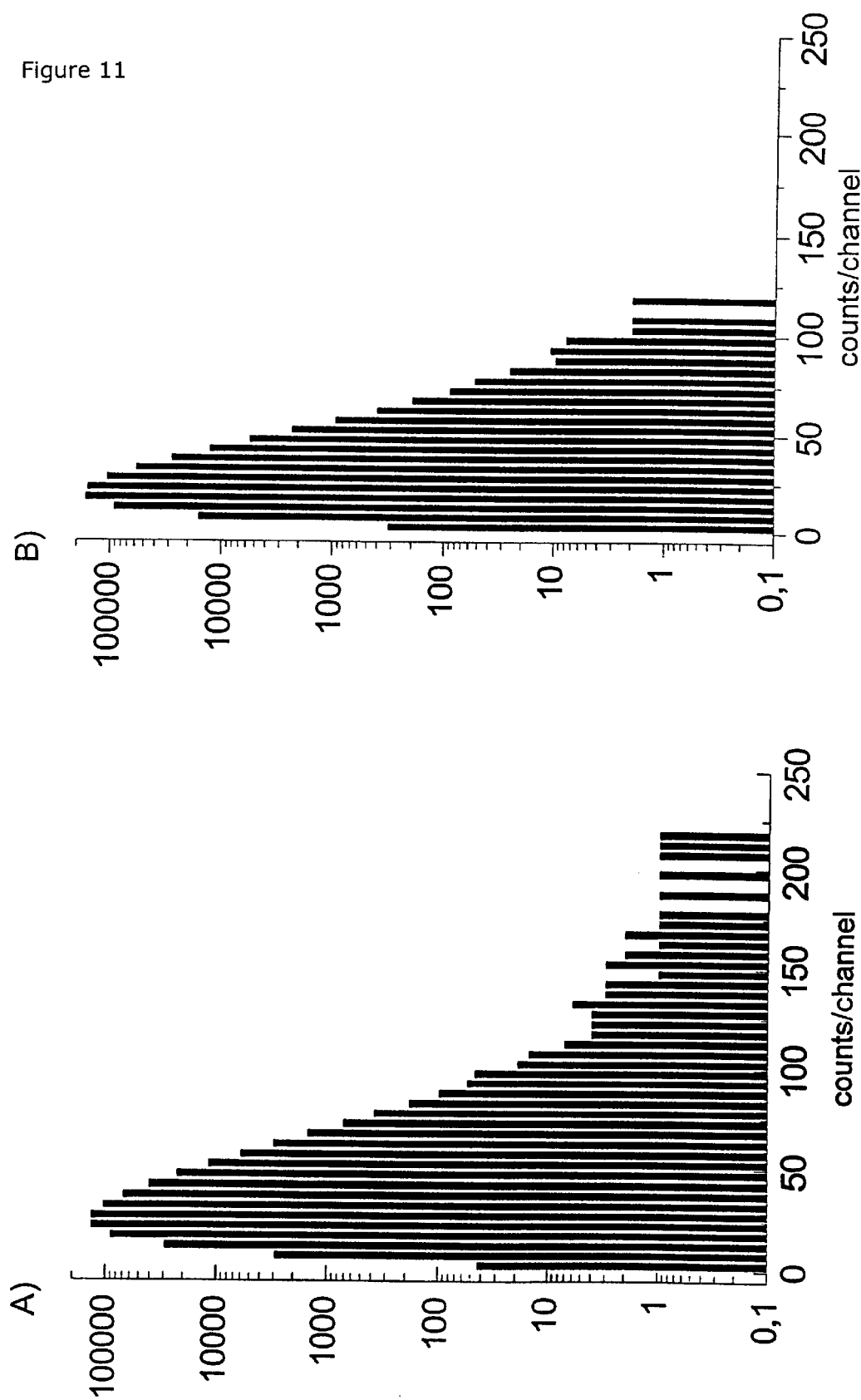
FIG. 11 shows the frequency distribution of the fluorescence photons for CJD-positive (left) and CJD-negative (right) samples of cerebrospinal fluid.

FIG. 11 shows the frequency distribution of the fluorescence photons per measuring channel for a channel width of 250 µs and concentration of the probe rPrP-Cy2=20 nM; left: CJD-positive cerebrospinal fluid sample, right: CJD-negative cerebrospinal fluid sample.

The height of the peaks represents the number of photons while the number of channels is a measure of the integral over the area of all peaks. In the CJD-positive samples, a higher proportion of large fluorescence peaks is observed. By setting a threshold value, a clear distinction can be made between CJD-positive and CJD-negative samples.

Figure 12:
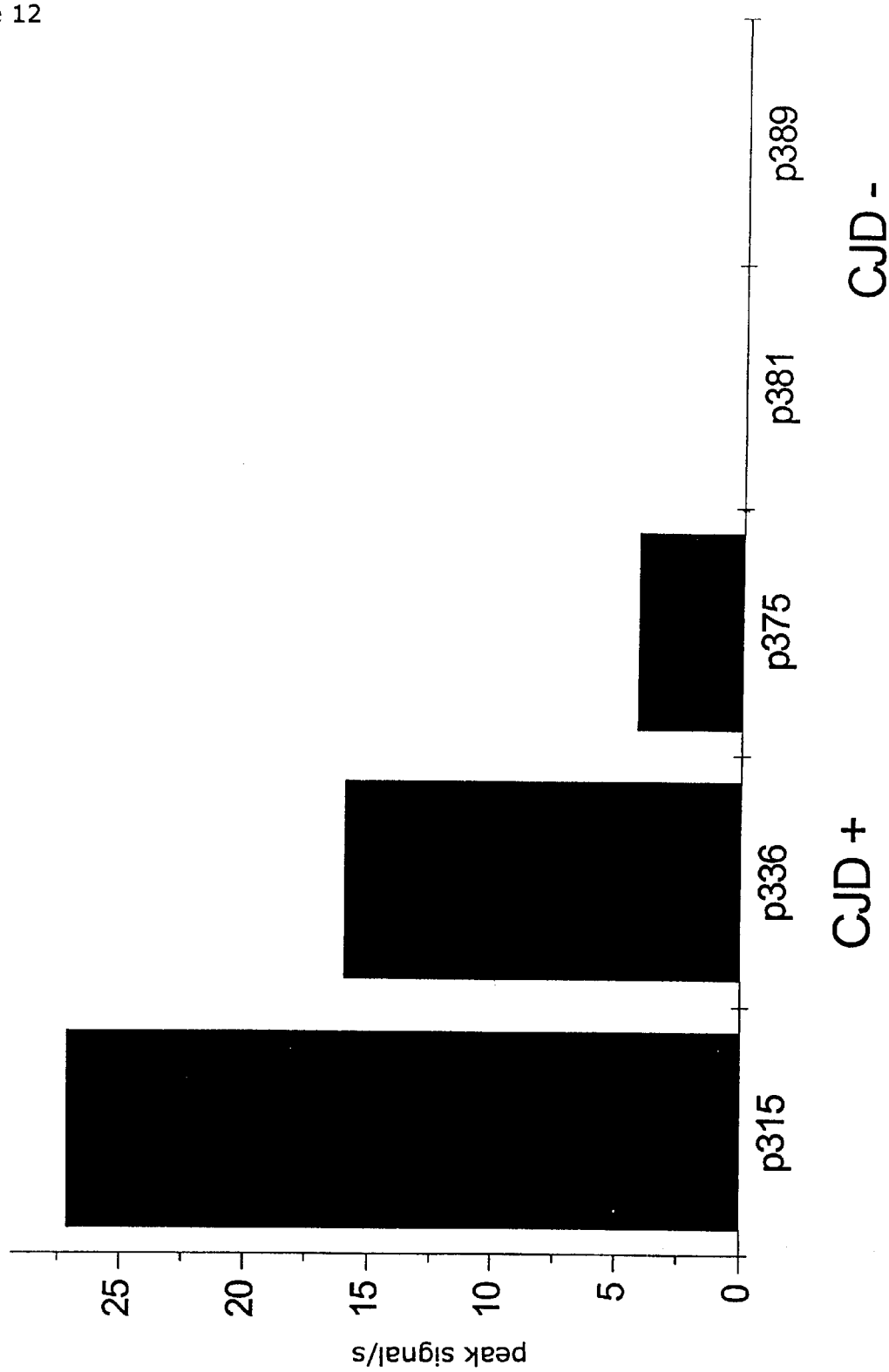
FIG. 12 shows the frequency of fluorescence photons from channels with more than 150 counts/channel in CJD-positive and CJD-negative samples of cerebrospinal fluid.

FIG. 12 shows the frequency of fluorescence photons from channels with more than 150 counts/channel in CJD-positive (CJD+)/CJD-negative (CJD−) cerebrospinal fluid samples at a channel width of 250 µs and a concentration of the probe rPrP-Cy2 of 20 nM. p315 etc. are internal identification numbers of the patients.

In the two-color design, a coincidence analysis can be made by multiplying the red by the green signal in order to recognize peaks from aggregates labeled with probes of both colors. By a refined peak-burst analysis, the separation of large peaks from the signal of the probe could be further improved.

EXAMPLE 11
Congo Red as a Model for the Screening Method

Congo red is known for its inhibiting effect on fibrillogenesis.

Figure 13:
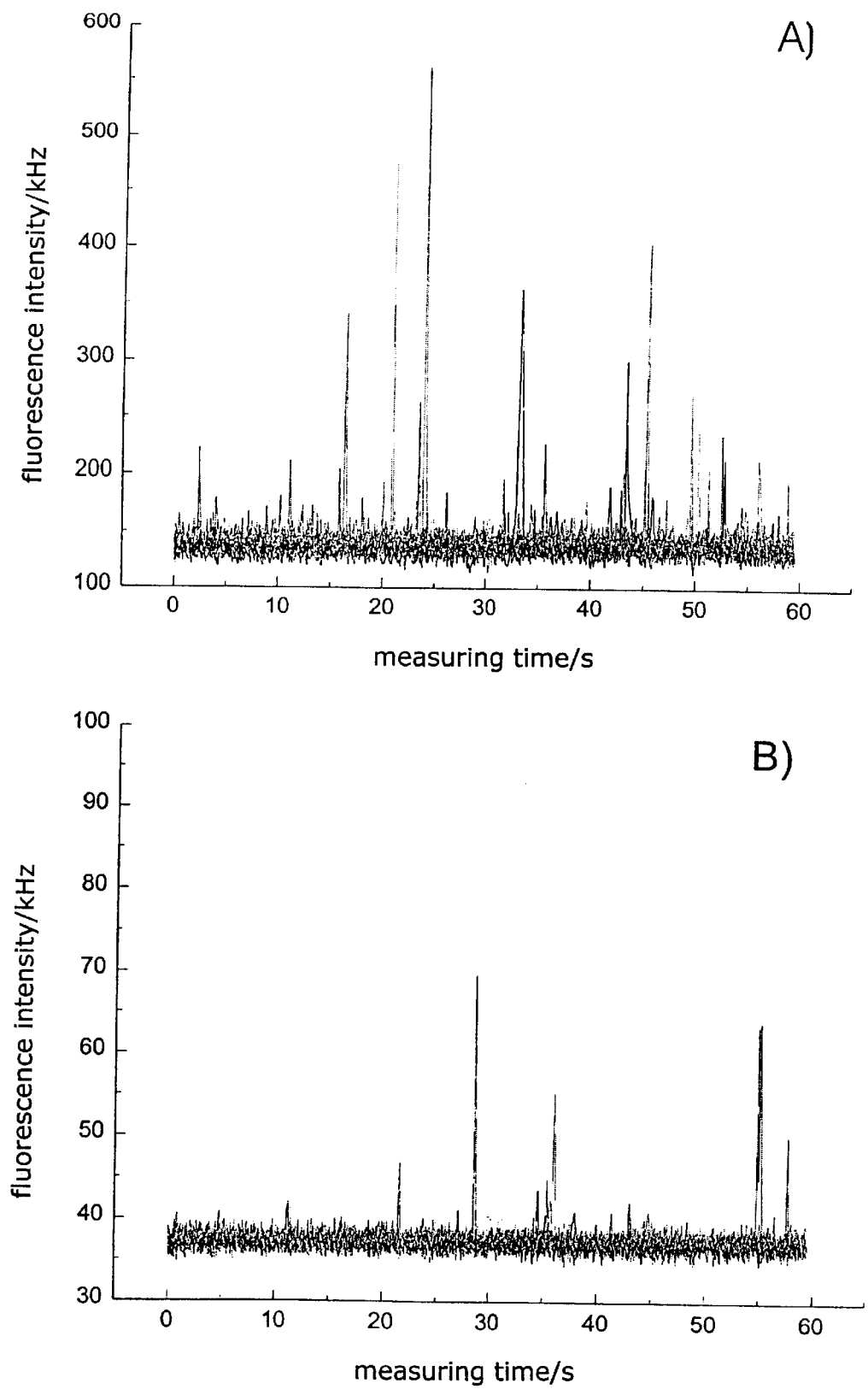
FIG. 13 shows the influence of Congo red on the association of the specific probe A$\beta$1-42CY2.

The original measurement (20 measurements each with one minute of measuring time) in the cerebrospinal fluid of a patient afflicted with Alzheimer's dementia is represented in FIG. 13.

FIG. 13 shows the influence of Congo red on the association of the specific probe Aβ-42-Cy2 to synthetic Aβ1-42 aggregates. In the FCS, a decrease of the signal intensity of the homologous association to 20% can be observed upon the addition of 1 mM Congo red.

Upon the addition of 1 mM Congo red (bottom), a significant decrease of the detectable peaks as compared to the control batch (top) can be observed. Because of the fact that Congo red absorbs in the range of the excitation wavelength, a different scaling of the measurement has been done for samples with and without Congo red.

This shows that substances which inhibit fibrillogenesis can be identified in FCS.

What is claimed is:

1. A method for the diagnostic detection of diseases associated with pathological protein depositions by measuring an association of substructures of the pathological protein depositions, structures forming pathological protein depositions, structures corresponding to pathological protein depositions and/or pathological protein depositions as a probe;
to substructures of the pathological protein depositions, structures forming pathological protein depositions, structures corresponding to pathological protein depositions and/or pathological protein depositions as targets;
characterized in that the target is detected in liquid phase; with the proviso that the association of the probe to the target is measured before self-aggregation of the probe predominates.

2. The method according to claim 1, wherein, for detecting Alzheimer's disease, the liquid phase is obtained from body fluids or is itself a body fluid.

3. The method according to claim 1, wherein said substructures of the pathological protein depositions, structures forming pathological protein depositions, structures corresponding to pathological protein depositions and/or pathological protein depositions have at least one detectable property.

4. The method according to claim 3, wherein said substructures of the pathological protein depositions having at least one detectable property are monomeric or oligomeric units of pathological protein depositions, or the substructures are homologous with monomeric or oligomeric units of pathological protein depositions.

5. The method according to claim 1, wherein said probe and target are derived from the same or from different types of pathological protein depositions.

6. The method according to claim 1, wherein said substructures can be obtained by treating pathological protein depositions with physical means.

7. The method according to claim 6, wherein the physical means are selected from the group consisting of ultrasonication, and the action of temperature changes.

8. The method according to claim 1, wherein said substructures can be obtained by treating pathological protein depositions with chemical means.

9. The method according to claim 8, wherein the chemical means are selected from the group consisting of treatment with solutions of different ionic strengths, treatment with solutions of chaotrophic ions, treatment with detergents, treatment with enzymes and combinations thereof.

10. The method of claim 9, wherein the enzymes are proteases.

11. The method according to claim 3, wherein said at least one detectable property is either intrinsic to the substructure, or it is introduced later.

12. The method according to claim 1, wherein other substances which will interact with the targets are used to increase the specificity or selectivity of the diagnostic detection.

13. The method according to claim 3, wherein said at least one detectable property size or dimension, molecular weight, structure, circular dichroism, optical properties, radioactivity or combinations thereof.

14. The method according to claim 13, wherein the optical properties are luminescence, flourescence, and/or absorption.

15. The method according to claim 3, wherein the measurement of said at least one detectable property is performed by physical methods.

16. The method of claim 15, wherein the physical methods are spectroscopic methods.

17. The method according to claim 3, wherein the measurement of said at least one detectable property is performed by fluorimetric methods.

18. The method according to claim 17, wherein the fluorimetric methods are selected from the group consisting of confocal fluorescence spectroscopy, and fluorescence correlation spectroscopy (FCS), FCS in combination with cross-correlation, with their respective appropriate evaluation methods.

19. The method according to claim 1, wherein said pathological protein depositions are amyloid plaques and/or neurofibrillar filaments (NFT) which are derived from the neuronal system and are associated with neurodegenerative diseases.

20. The method according to claim 19, wherein the neurodegenerative diseases are selected from the group consisting of Alzheimer's disease, transmissible spongiform encephalopathy, Huntington's chorea, Parkinson's disease, hereditary cerebral amyloid angiopathy.

21. The method according to claim 1, wherein said pathological protein depositions are amyloid plaques derived from organs other than the neuronal system and are associated with disease.

22. The method according to claim 21, wherein the diseases are selected from the group consisting of primary systemic amyloidosis (AL amyloidosis), reacrive systemic amyloidosis (AA amyloidosis), familial amyloid polyneuropahty, type II diabetes, injection-localized amyloidosis, medullary carcinoma of the thyroid gland, beta-2 microglobulin amyloidosis, hereditary non-neuropathic amyloidosis, and Finnish hereditary systemic amyloidosis.

23. The method according to claim 1, wherein said probes are recombinant proteins, protein fragments or peptides having sequence homologies with amyloid plaques and/or neurofibrillar filaments.

24. The method according to claim 1, wherein samples are taken from body fluids, or secretions or tissue and contacted with probes for the diagnostic detection of any diseases, incubated, and the association of the probes to targets is measured.

25. The method of claim 24, wherein the body fluids are slected from the group consisting of cerebrospinal fluid, blood, lymph, urine.

26. The method according to claim 24, wherein the secretions are sputum.

27. The method according to claim 3, wherein the parameters selected from the group consisting of translational diffusion rates, rotational diffusion rates, lifetimes of excited states, polarization of radiation, energy transfer, quantum yield, number of concentration of particles, and intensity differences are established from said at least one detectable property.

* * * * *